(12) United States Patent
Kohn et al.

(10) Patent No.: US 7,662,856 B2
(45) Date of Patent: Feb. 16, 2010

(54) COMPOSITIONS HAVING ANTIMYCROBIAL ACTIVITY INCLUDING A HYDROXAMATE OR A HYDROXAMATE AND A HYDROXLYAMINE

(75) Inventors: Harold Kohn, Chapel Hill, NC (US); Myoung Goo Kim, Summerfield, NC (US); Kurt L. Krause, Dunedin (NZ); James M. Briggs, Katy, TX (US); Michael Benedik, Bryan, TX (US); Ulrich Strych, Pearland, TX (US)

(73) Assignee: The University of Houston System, Houston, TX (US)

( * ) Notice: Subject to any disclaimer, the term of this patent is extended or adjusted under 35 U.S.C. 154(b) by 392 days.

(21) Appl. No.: 10/592,254

(22) PCT Filed: Aug. 30, 2004

(86) PCT No.: PCT/US2004/028124

§ 371 (c)(1), (2), (4) Date: Mar. 5, 2007

(87) PCT Pub. No.: WO2005/020973

PCT Pub. Date: Mar. 10, 2005

(65) Prior Publication Data

US 2008/0249181 A1    Oct. 9, 2008

Related U.S. Application Data

(60) Provisional application No. 60/499,174, filed on Aug. 29, 2003, provisional application No. 60/498,823, filed on Aug. 29, 2003.

(51) Int. Cl.
*A61K 31/135* (2006.01)
(52) U.S. Cl. ........................ 514/561; 514/645
(58) Field of Classification Search ................ 514/561, 514/645
See application file for complete search history.

(56) References Cited

OTHER PUBLICATIONS

Gale, Glen R., et al., "Further Studies of the Antimycobacterial Agents Glycyl Hydroxamic Acid and Beta-Alanyl Hydroxamic Acid", Canadian Journal of Microbiology, vol. 12, (1956).*

* cited by examiner

*Primary Examiner*—Raymond J Henley, III
(74) *Attorney, Agent, or Firm*—Robert W Strozier

(57) ABSTRACT

Antimycorbacterial compositions are disclosed comprising at least one hydroxamate or at least one hydroxamate and at least one hydroxylamine. The preferred ratio of hydroxamate to hydroxylamines is about 100:1 to about 1:1. A method for inhibiting mycobacterial growth is also disclosed comprising the step of administering the compositions of this invention to an animal including a human.

32 Claims, No Drawings

SEQUENCE LISTING

<160> NUMBER OF SEQ ID NOS: 2

<210> SEQ ID NO 1
<211> LENGTH: 357
<212> TYPE: PRT
<213> ORGANISM: Pseudomonas aeruginosa

<400> SEQUENCE: 1

```
Met Arg Pro Ala Arg Ala Leu Ile Asp Leu Gln Ala Leu Arg His Asn
1               5                   10                  15

Tyr Arg Leu Ala Arg Glu Ala Thr Gly Ala Arg Ala Leu Ala Val Ile
            20                  25                  30

Lys Ala Asp Ala Tyr Gly His Gly Ala Val Arg Cys Ala Glu Ala Leu
        35                  40                  45

Ala Ala Glu Ala Asp Gly Phe Ala Val Ala Cys Ile Glu Glu Gly Leu
    50                  55                  60

Glu Leu Arg Glu Ala Gly Ile Arg Gln Pro Ile Leu Leu Leu Glu Gly
65                  70                  75                  80

Phe Phe Glu Ala Ser Glu Leu Glu Leu Ile Val Ala His Asp Phe Trp
                85                  90                  95

Cys Val Val His Cys Ala Trp Gln Leu Glu Ala Ile Glu Arg Ala Ser
            100                 105                 110

Leu Ala Arg Pro Leu Asn Val Trp Leu Lys Met Asp Ser Gly Met His
        115                 120                 125

Arg Val Gly Phe Phe Pro Glu Asp Phe Arg Ala Ala His Glu Arg Leu
    130                 135                 140

Arg Ala Ser Gly Lys Val Ala Lys Ile Val Met Met Ser His Phe Ser
145                 150                 155                 160

Arg Ala Asp Glu Leu Asp Cys Pro Arg Thr Glu Glu Gln Leu Ala Ala
                165                 170                 175

Phe Ser Ala Ala Ser Gln Gly Leu Glu Gly Glu Ile Ser Leu Arg Asn
            180                 185                 190

Ser Pro Ala Val Leu Gly Trp Pro Lys Val Pro Ser Asp Trp Val Arg
        195                 200                 205

Pro Gly Ile Leu Leu Tyr Gly Ala Thr Pro Phe Glu Arg Ala His Pro
    210                 215                 220

Leu Ala Asp Arg Leu Arg Pro Val Met Thr Leu Glu Ser Lys Val Ile
225                 230                 235                 240

Ser Val Arg Asp Leu Pro Ala Gly Glu Pro Val Gly Tyr Gly Ala Arg
                245                 250                 255

Tyr Ser Thr Glu Arg Arg Gln Arg Ile Gly Val Val Ala Met Gly Tyr
            260                 265                 270

Ala Asp Gly Tyr Pro Arg His Ala Ala Asp Gly Thr Leu Val Phe Ile
        275                 280                 285

Asp Gly Lys Pro Gly Arg Leu Val Gly Arg Val Ser Met Asp Met Leu
    290                 295                 300

Thr Val Asp Leu Thr Asp His Pro Gln Ala Gly Leu Gly Ser Arg Val
305                 310                 315                 320

Glu Leu Trp Gly Pro Asn Val Pro Val Gly Ala Leu Ala Gln Phe
                325                 330                 335

Gly Ser Ile Pro Tyr Gln Leu Leu Cys Asn Leu Lys Arg Val Pro Arg
            340                 345                 350

Val Tyr Ser Gly Ala
```

<210> SEQ ID NO 2
<211> LENGTH: 382
<212> TYPE: PRT
<213> ORGANISM: Mycobacterium tuberculosis

<400> SEQUENCE: 2

```
Met Thr Pro Ile Ser Gln Thr Pro Gly Leu Leu Ala Glu Ala Met Val
 1               5                  10                  15

Asp Leu Gly Ala Ile Glu His Asn Val Arg Val Leu Arg Glu His Ala
            20                  25                  30

Gly His Ala Gln Leu Met Ala Val Lys Ala Asp Gly Tyr Gly His
        35                  40                  45

Gly Ala Thr Arg Val Ala Gln Thr Ala Leu Gly Gly Ala Ala Glu
    50                  55                  60

Leu Gly Val Ala Thr Val Asp Glu Ala Leu Ala Leu Arg Ala Asp Gly
65                  70                  75                  80

Ile Thr Ala Pro Val Leu Ala Trp Leu His Pro Pro Gly Ile Asp Phe
                85                  90                  95

Gly Pro Ala Leu Leu Ala Gln Val Ala Val Ser Ser Leu Arg Gln Leu
            100                 105                 110

Asp Glu Leu Leu His Ala Val Arg Arg Thr Gly Arg Thr Ala Thr Val
        115                 120                 125

Thr Val Lys Val Asp Thr Gly Leu Asn Arg Asn Gly Val Gly Pro Ala
    130                 135                 140

Gln Phe Pro Ala Met Leu Thr Ala Leu Arg Gln Ala Met Ala Glu Asp
145                 150                 155                 160

Ala Val Arg Leu Arg Gly Leu Met Ser His Met Val Tyr Ala Asp Lys
                165                 170                 175

Pro Asp Asp Ser Ile Asn Asp Val Gln Ala Gln Arg Phe Thr Ala Phe
            180                 185                 190

Leu Ala Gln Ala Arg Glu Gln Gly Val Arg Phe Glu Val Ala His Leu
        195                 200                 205

Ser Asn Ser Ser Ala Thr Met Ala Arg Pro Asp Leu Thr Phe Asp Leu
    210                 215                 220

Val Arg Pro Gly Ile Ala Val Tyr Gly Leu Ser Pro Val Pro Ala Leu
225                 230                 235                 240

Gly Asp Met Gly Leu Val Pro Ala Met Thr Val Lys Cys Ala Val Ala
                245                 250                 255

Leu Val Lys Ser Ile Arg Ala Gly Glu Gly Val Ser Tyr Gly His Thr
            260                 265                 270

Trp Ile Ala Pro Arg Asp Thr Asn Leu Ala Leu Leu Pro Ile Gly Tyr
        275                 280                 285

Ala Asp Gly Val Phe Arg Ser Leu Gly Gly Arg Leu Glu Val Leu Ile
    290                 295                 300

Asn Gly Arg Arg Cys Pro Gly Val Gly Arg Ile Cys Met Asp Gln Phe
305                 310                 315                 320

Met Val Asp Leu Gly Pro Gly Pro Leu Asp Val Ala Glu Gly Asp Glu
                325                 330                 335

Ala Ile Leu Phe Gly Pro Gly Ile Arg Gly Glu Pro Thr Ala Gln Asp
            340                 345                 350

Trp Ala Asp Leu Val Gly Thr Ile His Tyr Glu Val Val Thr Ser Pro
        355                 360                 365
```

-continued

```
Arg Gly Arg Ile Thr Arg Thr Tyr Arg Glu Ala Glu Asn Arg
        370             375             380
```

COMPOSITIONS HAVING ANTIMYCROBIAL ACTIVITY INCLUDING A HYDROXAMATE OR A HYDROXAMATE AND A HYDROXLYAMINE

RELATED APPLICATIONS

This application claims is a Nationalization of PCT/US04/28124 filed 30 Aug. 2004, which claims priority to U.S. Provisional Patent Application Ser. Nos. 60/499,174, filed 29 Aug. 2003 and 60/498,823 filed 29 Aug. 2003.

BACKGROUND OF THE INVENTION

1. Field of the Invention

This invention relates to a group of compounds with anti-mycobacterial activities that have a common hydroxamic acid structural feature and to methods for using same. This invention also relates to compositions including an hydroxamate and an hydroxylamine which possess anti-mycobacterial activity and to methods for making and using same.

More particularly, the present invention relates to compositions capable of inhibiting mycobacterium tuberculosis in standard mycobacterial growth assays, where the compositions include a therapeutically effective amount of an hydroxamate or an therapeutically effective amount of an hydroxamate and an hydroxylamine and to methods for using same.

2. Description of the Related Art

With the rapid evolution of bacterial resistance to antibiotic therapy there is a constant need for new generations of drugs, and to attain this there is a need for new targets on which to focus the development of antibiotics. As part of a computer based drug design project we are addressing the development of novel inhibitors of the alanine racemase from various pathogenic organisms. This enzyme is required for the biosynthesis of the cell wall of all bacteria including mycobacteria. Because humans do not contain an alanine racemase gene, and do not have a use for this product, d-alanine, it is a logical target for the development of specific antibacterial agents.

You are in receipt of a series of publications that relate to the medical use of hydroxamate compounds. They describe the study of similar agents in malaria, cancer, toxin deactivation, and as t-RNA synthetase inhibitors. Some of these publications specifically refer to the use of hydroxamic acid and related compounds against tuberculosis. These references include, but are not limited to the following papers: (1) Gale, G. R. and. Hynes, J. B., "Further studies of the antimycobacterial agents glycyl laydroxamic acid and ~-alanyl hydroxamie acid"(1966) Canadian J. Micro. (12), 73-81. (2) Gale, G. R. and Hawldns, J. E., "Antimycobacterial properties of glycyl hydroxamic acid and ~-alanyl hydroxamic acid", Am. Rev. Respiratory Dis. (92), 642-646.

Notably some of these compounds were shown in these reports to possess activity in animal models of tuberculosis and to lack significant toxicity. Following these types of studies it would be usual and customary to conduct confirmatory animal and toxicity studies. If these studies were promising, then human trials might be initiated. We have not as yet located the results of any further testing or trials for the compounds reported above.

Alanine racemase is necessary for cell wall biosynthesis in bacteria. Because humans do not have the alanine racemase gene and do not need the product it produces, it is a logical target for the development of specific antibacterial agents. Inhibitors of alanine racemase currently used (cycloserine) have neurological and other side effects because they are not specific to alanine racemase and inhibit the activity of other PLP-dependent enzymes. Cycloserine is currently used as a second-line drug against mycobacterium. Unfortunately, the use of cycloserine is limited because certain strains of mycobacterium have developed a resistance to it, and it has serious adverse effects including CNS toxicity and drug-induced psychosis. The need for new antibacterial agents that selectively inhibit only alanine racemase without causing side effects is obvious.

SUMMARY OF THE INVENTION

General Compositions

The present invention provides a composition having antimycobacterial activity including at least one hydroxamate.

The present invention provides a composition having antimycobacterial activity including at least one hydroxamate and at least one hydroxylamine.

The present invention provides a composition having antimycobacterial activity including a therapeutically effective amount of at least one hydroxamate.

The present invention provides a composition having antimycobacterial activity including a therapeutically effective amount of a combination of at least one hydroxamate and at least one hydroxylamine.

Specific Compositions

The present invention provides a composition having antimycobacterial activity including at least one compound of general formula (I):

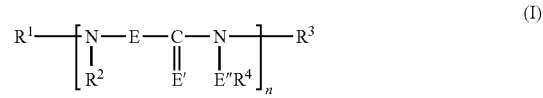

or pharmaceutically acceptable salts thereof, where:

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

The present invention provides a composition having antimycobacterial activity including at least one compound of general formula (I):

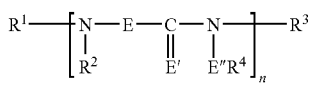

or pharmaceutically acceptable salts thereof and at least one hydroxylamine having the general formula (II):

   (II)

where:
- R is selected from the group consisting of an hydrogen atom, a C1 alkyl group, C2 alkyl group, C3 alkyl group and C4 alkyl group;
- $R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E' is selected from the group consisting of O, S, or $NR^7$;
- E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and
- n is an integer having a value between 1 and 4.

The present invention provides a composition having antimycobacterial activity including a therapeutically effective amount of at least one compound of general formula (I):

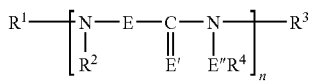

or pharmaceutically acceptable salts thereof, where:
- $R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E' is selected from the group consisting of O, S, or $NR^7$;
- E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and
- n is an integer having a value between 1 and 4.

The present invention provides a composition having antimycobacterial activity including a therapeutically effective amount of a combination of at least one compound of general formula (I):

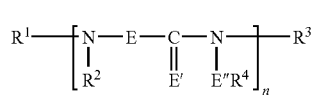

or pharmaceutically acceptable salts thereof and at least one hydroxylamine having the general formula (II):

   (II)

where:
- R is selected from the group consisting of an hydrogen atom, a C1 alkyl group, C2 alkyl group, C3 alkyl group and C4 alkyl group;
- $R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
- E' is selected from the group consisting of O, S, or $NR^7$;
- E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

General Method for Treating Tuberculosis and Other Mycobacterial Infections

The present invention provides a composition having anti-mycobacterial activity including at least one hydroxamate.

The present invention provides a composition having anti-mycobacterial activity including at least one hydroxamate and an hydroxylamine.

The present invention provides a composition having anti-mycobacterial activity including a therapeutically effective amount of at least one hydroxamate.

The present invention provides a composition having anti-mycobacterial activity including a therapeutically effective amount of a combination of at least one hydroxamate and at least one hydroxylamine.

Specific Methods for Treating Tuberculosis and Other Mycobacterial Infections

The present invention provides a method for treating tuberculosis and other mycobacterial infections in animals including humans including the step of administering to an animal including a human on an individual, continuous, periodic, or intermittent basis or protocol, a composition having anti-mycobacterial activity including at least one compound of general formula (I):

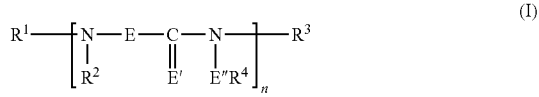

or pharmaceutically acceptable salts thereof, where:

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

The present invention also provides a method for treating tuberculosis and other mycobacterial infections in animals including humans including the step of administering to an animal including a human a composition having anti-mycobacterial activity including at least one compound of general formula (I):

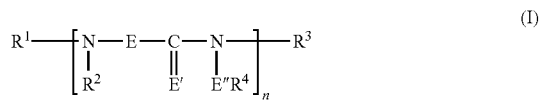

or pharmaceutically acceptable salts thereof and at least one hydroxylamine having the general formula (II):

where:

R is selected from the group consisting of an hydrogen atom, a C1 alkyl group, C2 alkyl group, C3 alkyl group and C4 alkyl group;

$R^1$, $R^2$, $R^3$ and $R^4$ are independently selected from the group consisting of hydrogen, linear or branched lower alkyl, linear or branched lower a alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic, lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

The present invention also provides a method for treating tuberculosis and other mycobacterial infections in animals including humans including the step of administering to an animal including a human a therapeutically effective amount of a compositions having anti-mycobacterial activity including at least one compound of general formula (I):

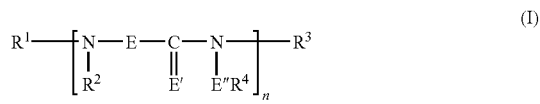

or pharmaceutically acceptable salts thereof wherein:

where:

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

The present invention also provides a method for treating tuberculosis and other mycobacterial infections in animals including humans including the step of administering to an animal including a human a therapeutically effective amount of a composition having anti-mycobacterial activity including a combination of at least one compound of general formula (I):

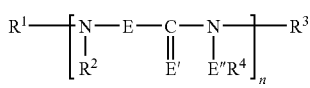

(I)

or pharmaceutically acceptable salts thereof and at least one hydroxylamine having the general formula (II):

(II)

where:

R is selected from the group consisting of an hydrogen atom, a C1 alkyl group, C2 alkyl group, C3 alkyl group and C4 alkyl group;

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

DETAILED DESCRIPTION OF THE INVENTION

The inventors have found that compounds based on a hydroxamic acid moiety are useful for the treatment of tuberculosis and other mycobacterial infections in animals including humans. The inventors have also found that combinations of those compounds with relatively small amount of hydroxyl amine having anti-mycobacterial activity and are useful for the treatment of tuberculosis and other mycobacterial infections in animals including humans.

The present invention broadly relates to compositions having anti-mycobacterial activity including between about 100 wt. % of at least one hydroxamate and about 0 wt. % of at least one hydroxylamine and about 50 wt. % of at least one hydroxamate and about 50 wt. % of at least one hydroxylamine. The hydroxamates can be optically pure, a racemic mixture of enantiomers, or an optically active mixture of enantiomers.

The present invention broadly relates to a method for treating mycobacteria including the step of administering a therapeutically effective amount of a composition including between about 100 wt. % of at least one hydroxamate and about 0 wt. % of at least one hydroxylamine and about 50 wt. % of at least one hydroxamate and about 50 wt. % of at least one hydroxylamine, where the at least one hydroxamate and at least one hydroxylamine can be co-administered or separately administered, with co-administration being preferred.

The administering step can be oral, inhalation, intravenous, intra-arterial, or mixtures or combinations of oral, inhalation, intravenous, or intra-arterial administrations. Preferably, the administering step is oral, inhalation and or mixtures or combinations of oral and inhalation administrations.

The hydroxamate compounds effective for use in this invention have the general formula (I):

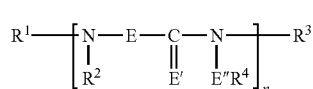

(I)

or pharmaceutically acceptable salts thereof, where:

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2R^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is $NR^7$, where $R^7$ is independently hydrogen, linear or branched lower alkyl, linear or branched lower alkenyl, linear or branched lower alkynyl, linear or branched aryl lower alkyl, linear or branched aryl, heterocyclic lower alkyl, linear or branched heterocyclic lower cycloalkyl, linear or branched lower cycloalkyl, linear or branched lower cycloalkyl lower alkyl, and mixtures or combinations thereof; and n is an integer having a value between 1 and 4.

$R^1$, $R^2$, $R^3$, $R^4$, $R^5$, $R^6$ and $R^7$ may be independently unsubstituted or substituted, if substituted the substituents comprise at least one electron withdrawing substituent or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

$R^8$, $R^9$ and $R^{10}$ may be independently unsubstituted or substituted with at least one electron withdrawing or at least one electron donating substituent as defined for $R^{1-7}$.

Preferred compounds of formula (I) are selected from the group consisting of glycine hydroxamic acid, glycine hydroxamic acid hydrochloride, glycine hydroxamic trifluoracetic acid, O-methylglycine hydroxamic acid trifluoroacetic acid, D-alanine hydroxamic acid hydrochloride, L-alanine hydroxamic acid hydrochloride, N-hydroxyoxalamide, sarcosine hydroxamic acid, D-methionine hydroxamic acid and mixtures or combinations thereof.

The hydroxylamine compounds effective for use in this invention have the general formula (II):

$$H_2N\text{---}OR \qquad (II)$$

where R is selected from the group consisting of an hydrogen atom, a C1 alkyl group, C2 alkyl group, C3 alkyl group and C4 alkyl group. Preferably, R is an hydrogen atom, a methyl group or an ethyl group. The preferred hydroxyamines are $H_2N$—OH, MeHN—OH or EtHN—OH.

The anti-mycobacterial composition comprising an anti-mycobacterial effective amount of at least one compound of the general formula (I), in the absence or present of a hydroxyl amine of the general formula (II) can also include a pharmaceutical acceptable carrier.

As used herein, the term "pharmaceutically acceptable carrier" means an inert, non toxic solid or liquid filler, diluent or encapsulating material, not reacting adversely with the active compound or with the patient. Suitable, liquid pharmaceutically acceptable carriers are well known in the art such as sterile water, saline, aqueous dextrose, sugar solutions, ethanol, glycols and or other similar carriers.

The formulations according to the invention may be administered as unit doses containing conventional non-toxic pharmaceutically acceptable carriers, diluents, adjuvants and vehicles which are typical for oral, inhalation, intravenous, or intra-arterial administration.

The compositions of this invention are administered to an animal including a human in the dose range between about 125 µg/mL and about 1 µg/mL for each hydroxamate or each hydroxylamine used in the compositions of this invention. Thus, for pure hydroxamate compositions, each hydroxamate is administered to an animal including a human in a dose range between about 125 µg/mL and about 1 µg/mL. While in a combination composition of at least one hydroxamate and at least one hydroxylamine, each hydroxamate and each hydroxylamine are administered to an an animal including a human in a dose range between about 125 µg/mL and about 1 µg/mL. Preferably, the ranges for each compound are independently between about 100 µg/mL and about 5 µg/mL. Particularly, the ranges for each compound are independently between about 100 µg/mL and about 25 µg/mL. The inventors have found that in the compositions including a combination of at least one hydroxamate and at least one hydroxylamine, the wt. % ratio of hydroxamate to hydroxylamine is generally between about 100:1 to about 1:1, preferably, between about 100:1 and 5:1 and particularly, between about 100:1 and about 10:1.

The inventors have tested several hydroxamates of this invention against M. tuberculosis, S. aureus, P. aeruginosa, and E. coli as set forth in Table A below. In Table A, In % refers to percent inhibition against the alanine racemase enzyme from each of the organisms; $K_i$ refers to the inhibition constant in mM against the alanine racemase enzyme from each of the organisms; and MIC stands for "minimum inhibitory concentration" and refers to the concentration of compound that inhibits the growth of bacteria in a culture grown under standardized conditions. Not shown in the results of Table A, is the inhibitory activity of these compounds to the growth of tuberculosis in a TB bacterial growth assay. The TB bacterial growth assay results are set forth in Table B. While many of these compounds are strong inhibitors of alanine racemase, the inventors do not know if their anti-mycobacterial activity is due solely, or even primarily to inhibition of this target enzyme. In fact, in inventors have become aware that the original hydroxamate compounds tested all includes a small amount (about 1 wt. % or less) of hydroxylamine. The inventors have since discovered that the hydroxamate compounds originally tested had a small amount of hydroxylamine as a contaminate. Although hydroxylamine is known to inhibit bacterial growth by complexing with alanine racemase, the amount of hydroxylamine (about 1 µg/mL) is well below the effective dose range known for hydroxylamine which is about 125 µg/mL. Thus, the combination of an hydroxamate and an hydroxylamine appear to have a synergistic anti-myco-bacterial activity.

The inventors have used the structure of two alanine racemases (ALR) to aid in the design to new drugs that may be operable in inhibiting these enzymes. The two enzymes are from Pseudomoinas aeruginosa and Mycobacteriun tuberculosis as set forth below:

```
Pseudomonas aeruginosa ALR (Seq. ID No. 1):

MRPARALIDLQALRHNYRLAREATGARALAVIKADAYGHGAVRCAEALAA

EADGFAVACIEEGLELREAGIRQPILLLEGFFEASELELIVAHDFWCVVH

CAWQLEAIERASLARPLNVWLKMDSGMHRVGFFPEDFRAAHERLRASGKV

AKIVMMSHFSRADELDCPRTEEQLAAFSAASQGLEGEISLRNSPAVLGWP

KVPSDWVRPGILLYGATPFERAHPLADRLRPVMTLESKVISVRDLPAGEP

VGYGARYSTERRQRIGVVAMGYADGYPRHAADGTLVFIDGKPGRLVGRVS
```

-continued
MDMLTVDLTDHPQAGLGSRVELWGPMVPVGALAAQFGSIPYQLLCNLKRV

PRVYSGA

*Mycobacterium tuberculosis* ALR (Seq. ID No. 2):
MTPISQTPGLLAEAMVDLGAIEHNVRVLREHAGHAQLMAVVKADGYGHGA

TRVAQTALGAGAAELGVATVDEALALRADGITAPVLAWLHPPGIDFGPAL

LAQVAVSSLRQLDELLHAVRRTGRTATVTVKVDTGLNRNGVGPAQFPAML

TALRQAMAEDAVRLRGLMSHMVYADKPDDSINDVQAQRFTAFLAQAREQG

VRFEVAHLSNSSATMARPDLTFDLVRPGIAVYGLSPVPALGDMGLVPAMT

VKCAVALVKSIRAGEGVSYGHTWIAPRDTNLALLPIGYADGVFRSLGGRL

EVLINGRRCPGVGRICMDQFMVDLGPGPLDVAEGDEAILFGPGIRGEPTA

QDWADLVGTIHYEVVTSPRGRITRTYREAENR

Novel Features

The compositions of this invention have been prepared and tested at a time of heightened interest in developing new therapies for tuberculosis. The compositions are novel because they are not related to any of the compounds currently in use to treat tuberculosis, with the possible exception of cycloserine. Since we also have the crystal structure of alanine racemase from tuberculosis, the structure can be use as an aid in the optimization of compound activity. Because these compounds have not been in clinical use, it is likely that the composition of this invention will be active against almost all strains, including drug resistant strains of tuberculosis.

The critical features of ALR that will aid in the development of improved anti-myco-bacterial compositions include the following atoms from the crystal structure of *Pseudomonas aeruginosa* ALR that relate to the active site of the enzyme:

| | | | | | | | | | |
|---|---|---|---|---|---|---|---|---|---|
| CRYST1 | 72.679 | 76.129 | 136.266 | 90.00 | 90.00 | 90.00 | C 2 2 21 | 4 | |
| SCALE1 | | 0.013759 | 0.000000 | 0.000000 | | 0.00000 | | | |
| SCALE2 | | 0.000000 | 0.013136 | 0.000000 | | 0.00000 | | | |
| SCALE3 | | 0.000000 | 0.000000 | 0.007339 | | 0.00000 | | | |
| ATOM | 1 | N1 | PLP | 358 | 5.890 | 25.908 | 17.398 | 1.000 | 16.57 |
| ATOM | 2 | C2 | PLP | 358 | 5.860 | 25.384 | 16.144 | 1.000 | 16.64 |
| ATOM | 3 | C2A | PLP | 358 | 5.833 | 23.858 | 15.961 | 1.000 | 15.86 |
| ATOM | 4 | C3 | PLP | 358 | 5.728 | 26.198 | 15.064 | 1.000 | 16.74 |
| ATOM | 5 | O3 | PLP | 358 | 5.626 | 25.679 | 13.823 | 1.000 | 18.80 |
| ATOM | 6 | C4 | PLP | 358 | 5.624 | 27.574 | 15.216 | 1.000 | 16.59 |
| ATOM | 7 | C5 | PLP | 358 | 5.652 | 28.096 | 16.527 | 1.000 | 16.37 |
| ATOM | 8 | C6 | PLP | 358 | 5.782 | 27.240 | 17.566 | 1.000 | 15.48 |
| ATOM | 9 | C5A | PLP | 358 | 5.480 | 29.604 | 16.770 | 1.000 | 16.20 |
| ATOM | 10 | OP4 | PLP | 358 | 4.086 | 29.941 | 16.633 | 1.000 | 16.19 |
| ATOM | 11 | P | PLP | 358 | 3.525 | 31.402 | 17.008 | 1.000 | 16.27 |
| ATOM | 12 | OP1 | PLP | 358 | 4.174 | 32.346 | 16.064 | 1.000 | 16.84 |
| ATOM | 13 | OP2 | PLP | 358 | 2.065 | 31.338 | 16.836 | 1.000 | 17.82 |
| ATOM | 14 | OP3 | PLP | 358 | 3.918 | 31.635 | 18.427 | 1.000 | 14.85 |
| ATOM | 15 | C4AA | PLP | 358 | 6.056 | 28.506 | 14.061 | 0.500 | 16.24 |
| ATOM | 16 | C4BB | PLP | 358 | 4.823 | 28.510 | 14.300 | 0.500 | 26.88 |
| ATOM | 17 | N | DLY | 359 | 3.417 | 26.795 | 12.294 | 1.000 | 48.57 |
| ATOM | 18 | CA | DLY | 359 | 3.917 | 27.532 | 11.149 | 1.000 | 27.53 |
| ATOM | 19 | C | DLY | 359 | 4.689 | 26.599 | 10.228 | 1.000 | 43.00 |
| ATOM | 20 | OT1 | DLY | 359 | 5.778 | 26.145 | 10.662 | 1.000 | 56.73 |
| ATOM | 21 | OT2 | DLY | 359 | 4.266 | 26.271 | 9.107 | 1.000 | 42.97 |
| ATOM | 22 | CB | DLY | 359 | 2.854 | 28.394 | 10.504 | 1.000 | 27.08 |
| ATOM | 23 | CG | DLY | 359 | 2.816 | 29.839 | 10.957 | 1.000 | 52.76 |
| ATOM | 24 | CD | DLY | 359 | 3.842 | 30.116 | 12.044 | 1.000 | 64.94 |
| ATOM | 25 | CE | DLY | 359 | 3.200 | 30.029 | 13.419 | 1.000 | 72.55 |
| ATOM | 26 | NZ | DLY | 359 | 3.562 | 28.764 | 14.116 | 1.000 | 61.63 |
| ATOM | 27 | N | MET | 1 | 18.287 | 57.694 | −3.207 | 1.000 | 29.47 |
| ATOM | 28 | CA | MET | 1 | 17.812 | 56.421 | −2.685 | 1.000 | 24.27 |
| ATOM | 29 | C | MET | 1 | 16.294 | 56.389 | −2.548 | 1.000 | 19.19 |
| ATOM | 30 | O | MET | 1 | 15.682 | 57.358 | −2.103 | 1.000 | 21.13 |
| ATOM | 31 | CB | MET | 1 | 18.456 | 56.139 | −1.325 | 1.000 | 30.26 |
| ATOM | 32 | CG | MET | 1 | 17.797 | 55.000 | −0.564 | 1.000 | 33.61 |
| ATOM | 33 | SD | MET | 1 | 18.979 | 53.704 | −0.153 | 1.000 | 44.73 |
| ATOM | 34 | CE | MET | 1 | 17.950 | 52.294 | 0.249 | 1.000 | 31.76 |
| ATOM | 35 | N | ARG | 2 | 15.665 | 55.245 | −2.812 | 1.000 | 18.73 |
| ATOM | 36 | CA | ARG | 2 | 14.263 | 55.112 | −2.465 | 1.000 | 17.06 |
| ATOM | 37 | C | ARG | 2 | 14.035 | 55.237 | −0.953 | 1.000 | 16.99 |
| ATOM | 38 | O | ARG | 2 | 14.758 | 54.626 | −0.180 | 1.000 | 17.64 |
| ATOM | 39 | CB | ARG | 2 | 13.812 | 53.752 | −2.933 | 1.000 | 19.81 |
| ATOM | 40 | CG | ARG | 2 | 12.363 | 53.440 | −3.086 | 1.000 | 20.60 |
| ATOM | 41 | CD | ARG | 2 | 12.128 | 52.127 | −3.844 | 1.000 | 19.07 |
| ATOM | 42 | NE | ARG | 2 | 10.706 | 51.722 | −3.737 | 1.000 | 18.62 |
| ATOM | 43 | CZ | ARG | 2 | 10.203 | 50.677 | −3.083 | 1.000 | 14.10 |
| ATOM | 44 | NH1 | ARG | 2 | 10.963 | 49.822 | −2.376 | 1.000 | 15.34 |
| ATOM | 45 | NH2 | ARG | 2 | 8.907 | 50.427 | −3.081 | 1.000 | 14.97 |
| ATOM | 46 | N | PRO | 3 | 13.058 | 56.003 | −0.475 | 1.000 | 16.64 |
| ATOM | 47 | CA | PRO | 3 | 12.883 | 56.212 | 0.971 | 1.000 | 16.35 |
| ATOM | 48 | C | PRO | 3 | 12.259 | 55.083 | 1.772 | 1.000 | 16.34 |
| ATOM | 49 | O | PRO | 3 | 12.098 | 55.184 | 2.996 | 1.000 | 21.50 |
| ATOM | 50 | CB | PRO | 3 | 12.033 | 57.493 | 1.009 | 1.000 | 16.82 |
| ATOM | 51 | CG | PRO | 3 | 11.229 | 57.444 | −0.241 | 1.000 | 16.82 |

-continued

| | | | | | | | | |
|---|---|---|---|---|---|---|---|---|
| ATOM | 52 | CD | PRO | 3 | 12.142 | 56.829 | −1.265 | 1.000 | 16.35 |
| ATOM | 53 | N | ALA | 4 | 11.947 | 53.947 | 1.181 | 1.000 | 14.96 |
| ATOM | 54 | CA | ALA | 4 | 11.341 | 52.821 | 1.871 | 1.000 | 15.34 |
| ATOM | 55 | C | ALA | 4 | 12.302 | 52.203 | 2.870 | 1.000 | 14.62 |
| ATOM | 56 | O | ALA | 4 | 13.483 | 52.046 | 2.539 | 1.000 | 16.72 |
| ATOM | 57 | CB | ALA | 4 | 10.965 | 51.796 | 0.820 | 1.000 | 17.08 |
| ATOM | 58 | N | ARG | 5 | 11.847 | 51.797 | 4.051 | 1.000 | 15.38 |
| ATOM | 59 | CA | ARG | 5 | 12.686 | 51.031 | 4.965 | 1.000 | 14.99 |
| ATOM | 60 | C | ARG | 5 | 11.840 | 50.367 | 6.026 | 1.000 | 14.32 |
| ATOM | 61 | O | ARG | 5 | 10.691 | 50.764 | 6.272 | 1.000 | 16.25 |
| ATOM | 62 | CB | ARG | 5 | 13.722 | 51.903 | 5.649 | 1.000 | 18.93 |
| ATOM | 63 | CG | ARG | 5 | 13.140 | 53.035 | 6.462 | 1.000 | 21.76 |
| ATOM | 64 | CD | ARG | 5 | 14.305 | 53.898 | 6.985 | 1.000 | 23.36 |
| ATOM | 65 | NE | ARG | 5 | 13.785 | 54.861 | 7.912 | 1.000 | 25.27 |
| ATOM | 66 | CZ | ARG | 5 | 14.522 | 55.670 | 8.678 | 1.000 | 30.80 |
| ATOM | 67 | NH1 | ARG | 5 | 15.840 | 55.668 | 8.643 | 1.000 | 34.01 |
| ATOM | 68 | NH2 | ARG | 5 | 13.925 | 56.509 | 9.500 | 1.000 | 42.52 |
| | | | ... portion of PDB file omitted ... | | | | | | |
| ATOM | 2727 | N | PRO | 351 | 15.513 | 48.173 | 2.901 | 1.000 | 15.90 |
| ATOM | 2728 | CA | PRO | 351 | 16.496 | 47.975 | 3.960 | 1.000 | 15.31 |
| ATOM | 2729 | C | PRO | 351 | 15.862 | 47.730 | 5.331 | 1.000 | 14.58 |
| ATOM | 2730 | O | PRO | 351 | 14.835 | 48.314 | 5.641 | 1.000 | 16.93 |
| ATOM | 2731 | CB | PRO | 351 | 17.246 | 49.311 | 4.012 | 1.000 | 17.92 |
| ATOM | 2732 | CG | PRO | 351 | 16.845 | 50.112 | 2.840 | 1.000 | 19.24 |
| ATOM | 2733 | CD | PRO | 351 | 15.554 | 49.521 | 2.317 | 1.000 | 15.27 |
| ATOM | 2734 | N | ARG | 352 | 16.530 | 46.904 | 6.153 | 1.000 | 15.45 |
| ATOM | 2735 | CA | ARG | 352 | 16.182 | 46.680 | 7.535 | 1.000 | 14.79 |
| ATOM | 2736 | C | ARG | 352 | 17.214 | 47.392 | 8.423 | 1.000 | 15.43 |
| ATOM | 2737 | O | ARG | 352 | 18.405 | 47.110 | 8.306 | 1.000 | 17.05 |
| ATOM | 2738 | CB | ARG | 352 | 16.107 | 45.196 | 7.917 | 1.000 | 17.79 |
| ATOM | 2739 | CG | ARG | 352 | 14.884 | 44.533 | 7.270 | 1.000 | 21.42 |
| ATOM | 2740 | CD | ARG | 352 | 14.826 | 43.057 | 7.563 | 1.000 | 22.14 |
| ATOM | 2741 | NE | ARG | 352 | 16.007 | 42.379 | 7.024 | 1.000 | 24.75 |
| ATOM | 2742 | CZ | ARG | 352 | 16.108 | 41.064 | 6.937 | 1.000 | 21.96 |
| ATOM | 2743 | NH1 | ARG | 352 | 15.103 | 40.316 | 7.342 | 1.000 | 22.29 |
| ATOM | 2744 | NH2 | ARG | 352 | 17.160 | 40.434 | 6.462 | 1.000 | 30.10 |
| ATOM | 2745 | N | VAL | 353 | 16.684 | 48.329 | 9.199 | 1.000 | 15.42 |
| ATOM | 2746 | CA | VAL | 353 | 17.532 | 49.153 | 10.054 | 1.000 | 14.57 |
| ATOM | 2747 | C | VAL | 353 | 17.265 | 48.779 | 11.500 | 1.000 | 14.52 |
| ATOM | 2748 | O | VAL | 353 | 16.192 | 49.007 | 12.011 | 1.000 | 16.43 |
| ATOM | 2749 | CB | VAL | 353 | 17.293 | 50.661 | 9.786 | 1.000 | 16.74 |
| ATOM | 2750 | CG1 | VAL | 353 | 18.267 | 51.473 | 10.621 | 1.000 | 19.72 |
| ATOM | 2751 | CG2 | VAL | 353 | 17.435 | 50.941 | 8.302 | 1.000 | 22.47 |
| ATOM | 2752 | N | TYR | 354 | 18.221 | 48.143 | 12.158 | 1.000 | 14.94 |
| ATOM | 2753 | CA | TYR | 354 | 18.111 | 47.660 | 13.517 | 1.000 | 16.61 |
| ATOM | 2754 | C | TYR | 354 | 18.477 | 48.773 | 14.511 | 1.000 | 17.12 |
| ATOM | 2755 | O | TYR | 354 | 19.434 | 49.531 | 14.345 | 1.000 | 20.50 |
| ATOM | 2756 | CB | TYR | 354 | 18.984 | 46.409 | 13.732 | 1.000 | 15.78 |
| ATOM | 2757 | CG | TYR | 354 | 18.537 | 45.287 | 12.828 | 1.000 | 15.23 |
| ATOM | 2758 | CD1 | TYR | 354 | 17.571 | 44.377 | 13.216 | 1.000 | 15.73 |
| ATOM | 2759 | CD2 | TYR | 354 | 19.090 | 45.186 | 11.561 | 1.000 | 16.56 |
| ATOM | 2760 | CE1 | TYR | 354 | 17.192 | 43.379 | 12.338 | 1.000 | 14.50 |
| ATOM | 2761 | CE2 | TYR | 354 | 18.715 | 44.192 | 10.690 | 1.000 | 18.11 |
| ATOM | 2762 | CZ | TYR | 354 | 17.765 | 43.294 | 11.099 | 1.000 | 17.22 |
| ATOM | 2763 | OH | TYR | 354 | 17.359 | 42.288 | 10.256 | 1.000 | 18.94 |
| ATOM | 2764 | N | SER | 355 | 17.672 | 48.840 | 15.568 | 1.000 | 16.89 |
| ATOM | 2765 | CA | SER | 355 | 18.007 | 49.645 | 16.722 | 1.000 | 20.52 |
| ATOM | 2766 | C | SER | 355 | 17.977 | 48.806 | 17.995 | 1.000 | 20.37 |
| ATOM | 2767 | O | SER | 355 | 17.297 | 47.796 | 18.086 | 1.000 | 20.84 |
| ATOM | 2768 | CB | SER | 355 | 17.056 | 50.820 | 16.872 | 1.000 | 22.59 |
| ATOM | 2769 | OG | SER | 355 | 15.778 | 50.355 | 17.249 | 1.000 | 32.04 |
| ATOM | 2770 | N | GLY | 356 | 18.726 | 49.230 | 19.000 | 1.000 | 22.99 |
| ATOM | 2771 | CA | GLY | 356 | 18.698 | 48.525 | 20.275 | 1.000 | 23.83 |
| ATOM | 2772 | C | GLY | 356 | 19.620 | 47.327 | 20.321 | 1.000 | 25.32 |
| ATOM | 2773 | O | GLY | 356 | 19.512 | 46.472 | 21.211 | 1.000 | 34.87 |
| ATOM | 2774 | N | ALA | 357 | 20.569 | 47.203 | 19.393 | 1.000 | 27.11 |
| ATOM | 2775 | CA | ALA | 357 | 21.436 | 46.025 | 19.422 | 1.000 | 42.24 |
| ATOM | 2776 | C | ALA | 357 | 22.377 | 45.978 | 20.628 | 1.000 | 45.72 |
| ATOM | 2777 | O | ALA | 357 | 22.787 | 47.023 | 21.163 | 1.000 | 38.82 |
| ATOM | 2778 | CB | ALA | 357 | 22.226 | 45.967 | 18.121 | 1.000 | 46.64 |
| ATOM | 2779 | OT2 | ALA | 357 | 22.708 | 44.837 | 21.025 | 1.000 | 58.13 |
| | | | ... portion of PDB file omitted ... | | | | | | |
| ATOM | 3089 | OW0 | WAT | 839 | 10.655 | 56.476 | 12.115 | 1.000 | 42.28 |
| ATOM | 3090 | OW0 | WAT | 840 | 2.151 | 47.888 | 23.618 | 1.000 | 47.09 |
| ATOM | 3091 | OW0 | WAT | 842 | 20.550 | 51.874 | 14.686 | 1.000 | 33.45 |
| ATOM | 3092 | OW0 | WAT | 843 | 22.114 | 9.974 | 2.401 | 1.000 | 44.24 |
| ATOM | 3094 | OW0 | WAT | 845 | 6.672 | 70.712 | −6.117 | 1.000 | 37.20 |
| ATOM | 3095 | OW0 | WAT | 846 | 22.893 | 9.953 | 7.913 | 1.000 | 48.39 |
| ATOM | 3096 | OW0 | WAT | 847 | 19.552 | 31.453 | 30.000 | 1.000 | 43.42 |

-continued

| ATOM | 3097 | OW0 | WAT | 848 | −8.507 | 12.416 | 25.018 | 1.000 | 46.62 |
| ATOM | 3098 | OW0 | WAT | 851 | 13.421 | −0.795 | 19.395 | 1.000 | 42.34 |

The critical features of *Mycobacterium tuberculosis* ALR are similar and can also aid in the design of new anti-mycobacterial compositions.

Hydroxamates: General Preparation and Purification

The hydroxamates of this invention are relatively simple to prepare and purify. For the most part, the hydroxamates of this invention appear to be stable over time. The hydroxamates of this invention are also novel because they are active against mycobacteria, but not Gram positive or Gram negative bacteria. As a result, the hydroxamates of this invention are not likely to cause side adverse effects such as the elimination of normal bacterial populations in the treated host.

Testing has been done for a number of compounds of general formula (I) as inhibitors of alanine racemase and as inhibitors of bacterial growth. The results of this testing are shown in the Tables A, B and C. Note that several of the compounds are strong inhibitors of alanine racemase. Note that, in growth assays, the compounds possess no appreciable activity against *S. aureus, P. aeruginosa,* and *E. coli,* but several possess activity against *M. tuberculosis* that approximates the activity of cycloserine. Please note that although many of these compounds are strong inhibitors of alanine racemase, we do not know if their anti-mycobacterial activity is due solely, or even primarily to inhibition of this target. For that further testing will be required.

the indicated hydroxamate with an approximate 1 wt. % hydroxylamine contaminant, which was discovered after the original testing results were obtained. The inventors believe that the two compounds, the hydroxamate and the hydroxylamine, work in a synergistic manner to inhibit mycobacterial growth, because hydroxylamine is effect at doses of about 100 µg/mL, while the compositions of this invention show anti-mycobacterial activity an hydroxylamine doses of $\geq 1$ µg/mL.

TABLE A

Inhibition and MIC data (% Inhibition at 2.5 mM, Ki [mM] and MIC[mM])

| Structure | *M. tuberculosis* In % | $K_i$ | *S. aureus* In % | $K_i$ | MIC | *P. aeruginosa* In % | $K_i$ | *E. Coli* In % | $K_i$ | MIC | Remark |
|---|---|---|---|---|---|---|---|---|---|---|---|
| $H_2NCH_2C(O)NHOH$ | 100 ± 1 | 0.008 | 91 ± 3 | 0.090 | >0.5 | 94 ± 1 | 0.065 | 90 ± 5 | 0.039 | >5 | Free base |
| $H_2NOH_2G(O)NHOH$ | 100 ± 2 | 0.031 | 92 ± 3 | 0.034 | >5 | 90 ± 2 | 0.033 | 90 ± 4 | 0.075 | >5 | Add 1 eq of TFA |
| $H_{-1}H_2NGH_a(O)NHOH$ | 105 ± 6 | 0.195 | 95 ± 1 | 0.217 | >5 | 114 ± 14 | 0.201 | 88 ± 4 | 0.268 | >5 | I-ICI salt |
| $TFA \cdot H_2NCH_2G(O)NHOH$ | 104 ± 4 | 0.022 | 99 ± 3 | 0.023 | >5 | 112 ± 7 | 0.020 | 94 ± 4 | 0.078 | >5 | TFA salt |
| $TFA \cdot H_2NGH_2G(O)N(GH_a)OH$ | 60 ± 3 | 0.786 | 57 ± 3 | 0.840 | >5 | 62 ± 4 | 0.802 | 52 ± 3 | 0.866 | >5 | |
| $TFA \cdot H_2NGH_2C(O)NHOCH_3$ | 66 | 1.386 | 47 | 1.845 | >5 | 55 | 1.507 | 67 | 1.337 | >5 | |
| $TFA \cdot H_2N\_H_{2-}(O)N(GH_a)OGHa$ | 66 ± 4 | 0.644 | 66 ± 3 | 0.590 | >5 | 68 ± 5 | 0.633 | 49 ± 2 | 0.875 | >5 | |
| $HzNGH(\sim Ha)G(O)NHOH$ | 48 ± 9 | 0.867 | 57 ± 4 | 0.810 | >5 | 66 ± 3 | 0.656 | 58 ± 2 | 0.756 | >5 | DL-alanine |
| $HGI \cdot H\sim NGH(OHa)O(O)NHOH$ | 70 ± 11 | 0.705 | 33 ± 6 | 2.675 | >5 | 29 ± 6 | 1.011 | 35 ± 7 | 5.204 | >5 | D-isomer |
| $HGI \cdot HaNGH(GHa)G(O)NHOH$ | 59 ± 7 | 0.689 | 32 ± 8 | 1.299 | >5 | 33 ± 2 | 1.060 | 39 ± 8 | 2.780 | >5 | L-isomer |
| $H_2NC(O)NHOH$ | 22 ± 8 | ND | 12 ± 7 | ND | >5 | 10 ± 4 | ND | 0 ± 12 | ND | >5 | |
| $Hg1HzNGHz\sim Hzg(O)NHOH$ | 79 ± 12 | 0.629 | 49 ± 12 | 0.401 | >5 | 34 ± 9 | 0.894 | 37 ± 10 | 1.206 | >5 | L-alanine |
| $H_2NC(O)C(O)NHOH$ | 93 ± 8 | 0.032 | 97 ± 0 | 0.017 | >5 | 99 ± 4 | 0.016 | 97 ± 4 | 0.052 | >5 | Oxamic acid |
| $CH_3NHCH_2C(O)NHOH$ | 81 ± 7 | 1.386 | 28 ± 5 | 14.345 | >5 | 24 ± 5 | 18.165 | 34 ± 12 | 5.696 | >5 | |
| $H_2NCH(CH_2OH)C(O)NHOH$ | 33 ± 8 | 3.20 | 19 ± 8 | 7.20 | >5 | 28 ± 5 | 5.10 | 0 ± 4 | ND | >5 | DL-serine |
| $TFA \cdot HzNCH(CH_2OH)C(O)N\ HOCH_3$ | 48 ± 10 | ND | 55 ± 2 | ND | ND | 24 ± 5 | ND | 28 ± 12 | ND | ND | DL-serine |
| $H_2NCH(CH_2CHaSCH_3)C(O)NHOH$ | 0 ± 4 | ND | 1 ± 3 | ND | >5 | 7 ± 4 | ~D | 0 ± 6 | ND | ND | DL-methionin |
| $PhCH_2NHGH_2C(O)NHOH$ | 88 ± 3 | 0.519 | 53 ± 13 | 1.976 | >5 | 39 ± 9 | 1.243 | 0.58 ± 3 | 1.838 | >5 | |
| $H_2NCH(CH_2OCONH_2)C(O)NILIOH$ | 97 ± 5 | 0.030 | 93 ± 4 | 0.056 | >5 | 94 ± 5 | 0.030 | 96 ± 8 | 0.008 | >5 | |
| D-cycloserine | 93 | 0.01 | 94 | 0.01 | 0.2 | 95 | 0.01 | 93 | 0.01 | | Control |

Results

The testing results are listed in the following tables for the indicated hydroxamate compounds. These test results include

TABLE B

TB Assay of Hydroxamate Candidates

| Compound | % In in TB-ALR-assay | Days of Detection |
|---|---|---|
| DMSO | 0 | 7 |
| Water | 0 | 8 |
| $HCl \cdot H_2NCH_2CH_2C(O)NHOH$ | 79 | 8.5 |
| $TFA \cdot H_2NCH_2C(O)N(CH_3)OH$ | 60 | 9 |
| $TFA \cdot H_2NCH_2C(O)N(CH_3)OCH$ | 66 | 9 |
| $H_2NC(O)NHOH$ | 22 | 9 |
| $TFA \cdot H_2NCH(CH_2OH)C(O)NHOCH_3$ | 48 | 9 |
| $HCl \cdot H_2NCH_2(O)NHOH$ | 100 | 16.5 |
| $HCl \cdot H_2NCH(CH_3)C(O)NHOH^*$ | 59 | 17.5 |
| $PhCH_2NHCH_2C(O)NHOH$ | 88 | 18.5 |
| $H_2NCH(CH_2OH)C(O)NHOH$ | 33 | 21.5 |
| $Hcl \cdot H_2NCH(CH_3)C(O)NHOH$ | 70 | 22.5 |
| $H_2NC(O)C(O)NHOH$ | 93 | 32 |
| $CH_3NHCH_2C(O)NHOH$ | 81 | 32.5 |
| $H_2NCH_2C(O)NHOH$ | 100 | >40 |
| $TFA \cdot H_2NCH_2C(O)NHOCH_3$ | 66 | >40 |

TABLE B-continued

TB Assay of Hydroxamate Candidates

| Compound | % In in TB-ALR-assay | Days of Detection |
|---|---|---|
| $H_2NCH(CH_2CH_2SCH_3)C(O)NHOH$ | 0 | >40 |
| D-Cycloserine | 96 | >40 |

TABLE C

Result of MGIT Assay

| Compound | MIC [µg/ml] |
|---|---|
| $TFA \cdot H_2NCH_2C(O)NHOCH_3$ | 50 |
| $H_2NCH_2C(O)NHOH$ | 50 |
| $H_2NC(O)C(O)NHOH$ | 50 |
| $CH_3NHCH_2C(O)NHOH$ | 200 |
| $HCl \cdot H_2NCH(CH_3)C(O)NHOH$ | 100 |
| $HCl \cdot H_2NCH(CH_3)C(O)NHOH$ | 50 |
| $HCl \cdot H_2NCH_2C(O)NHOH$ | 200 |
| $H_2NCH(CH_2OH)C(O)NHOH$ | 100 |
| $PhCH_2NHCH_2C(O)NHOH$ | 50 |
| $H_2NC(O)NHOH$ | >200 |
| $HCl \cdot H_2NCH_2CH_2C(O)NHOH$ | >200 |
| $HCl \cdot H_2NCH_2CH_2C(O)NHOH$ | >200 |
| $TFA \cdot H_2NCH(CH_2OH)C(O)NHOCH_3$ | >200 |
| $TFA \cdot H_2NCH_2C(O)N(CH_3)OCH_3$ | >200 |
| D-Cycloserine | <12.5 |

EXPERIMENTAL SECTION

General Method

Melting points were determined with a Thomas-Hoover melting point apparatus and were uncorrected. $^1H$ and $^{13}C$ NMR spectra were taken on a Varian VXR 300 and Bruker DRX z100 NMR instruments. Chemical shifts (b) are in parts per million (ppm) relative to tetramethylsilane, and coupling constants (J values) are in Hertz. Low- and high-resolution (CI) mass spectral investigations were conducted at the University of Texas at Austin by Dr. M. Moini. The low-resolution mass studies were run on a Finnegan MAT-TSQ-70 instrument and the high, resolution mass studies were conducted on a Micromass ZAB-E spectrometer. The solvents and reactants were of the best commercial grade available and were used without further purification unless noted. Thin-layer chromatography was run on precoated silica gel GHLF (10×20 cm; Aldrich No. Z27428-3).

General Coupling Procedure Using CDI for the BOC-Hydroxamie Acids (13-18, 22)

A solution of the butoxycarbonyl (BOC)-amino acid (1 equiv) in dry tetrahydrofuran (THF) (1.0-1.5 mL/1 mmol of BOC-amino acid) was added to a solution of carbonyldiimi-dazole (1 equiv) in a dry THF (3.0 mL/1 mmol of CDI). The reaction solution was stirred at room temperature (30 min), heated to reflux (30 rain), and cooled to room temperature. The desired hydroxylalrfine (1 equiv) was added to the reaction and the suspension was stirred (12-18 h). The solid was filtered and the filtrate diluted with ethylacetate (EtOAc) (10 mL), and washed successively with aqueous 2 N HCl (5 mL), saturated aqueous $NaHCO_3$ solution (10 mL), and H20 (5 mL). The EtOAc layer was dried magnesium sulfate ($MgSO_4$) and concentrated in vacuo. The residue was purified by PTLC (5-10% MeOH—$CHCl_3$) to afford the desired hydroxamic acid, where MeOH represent methanol.

N-(tert-Butoxycarbonyl)glycine Hydroxamic Acid (13)

Yield, 42%; $R_f$=0.35 (10% MeOH—$CHCl_3$); mp 117-119° C. (lit.[1]) mp 115-117° C.); $^1H$ NMR ($CD_3OD$, 300 MHz) δ1.44 (s, 9H), 3.66 (s, 2H); $^{13}C$ NMR ($CD_3OD$, 75 MHz) δ28.7 (3 C), 42.6, 80.8, 158.4, 169.5; MS (+CI) 191 [M+1]$^+$; $M_r$(+CI) 191.103 29 [M+1]$^+$ (calcd for $C_7H_{15}N_2O_4$, 191.103 18).

N'-Methyl-N-(tert-butoxycarbonyl)glycine Hydroxamic Acid (14)

Yield, 28%; $R_f$=0.65 (10% MeOH—$CHCl_3$); mp 98-100° C.; $^1H$ NMR ($CD_3OD$, 300 MHz) δ1.44 (s, 9H), 3.19 (s, 3H), 3.98 (s, 2H); $^{13}C$ NMR ($CD_3OD$, 75 MHz) δ28.7 (3 C), 36.5, 42.3, 80.5, 158.7, 171.8.

O-Methyl-N-(tert-butoxycarbonyl)glycine Hydroxamic Acid (15)

Yield, 35% as a semi-solid; $R_f$=0.56 (10% MeOH—$CHCl_3$); $^1H$ NMR ($CD_3OD$, 300 MHz) δ1.45 (s, 9H), 3.64 (s, 2H), 3.69 (s, 3H); $^{13}C$ NMR ($CD_3OD$, 75 MHz) δ28.7 (3 C), 42.7, 64.4, 80.8, 158.4, 169.4; MS (+CI) 205 [M+1]$^+$; $M_r$(+CI) 205.117 88 [M+1]$^+$ (calcd for $C_8H_{17}N_2O_4$, 205.118 83).

N-(tert-Butoxycarbonyl)-D-alanine Hydroxamic Acid (16)

Yield, 27%; $R_f$=0.37 (10% MeOH—$CHCl_3$); mp 115-117° C.; $^1H$ NMR ($CD_3OD$, 300 MHz) δ1.29 (d, J=7.2 Hz, 3H), 1.43 (s, 9H), 4.00 (q, J=7.2 Hz, 1H); $^{13}C$ NMR ($CD_3OD$, 75 MHz) δ18.6, 28.7 (3 C), 49.4, 80.6, 157.5, 172.7.

N-(tert-Butoxycarbonyl)-L-alanine Hydroxamic Acid (17)

Yield, 28%; $R_f$=0.37 (10% MeOH—$CHCl_3$); mp 116-118° C.; $^1H$ NMR ($CD_3OD$, 300 MHz) δ1.29 (d, J=7.2 Hz, 3H), 1.43 (s, 9H), 4.00 (q, J=7.2 Hz, 1H); $^{13}C$ NMR ($CD_3OD$, 75 MHz) δ18.6, 28.7 (3 C), 49.4, 80.6, 157.5, 172.7.

N-(tert-Butoxycarbonyl)-β-alanine Hydroxamic Acid (18)

Yield, 25%; $R_f$=0.28 (10% MeOH—$CHCl_3$); mp 85-87° C.; IR (KBr) 3323, 3239, 3062, 2977, 1687, 1634, 1540, 1431, 1368, 1292, 1179, 1037 cm$^{-1}$; $^1H$ NMR ($CD_3OD$, 300 MHz) δ1.42 (s, 9H), 2.27 (t, J=6.6 Hz, 2H), 3.30 (t, J=6.6 Hz, 2H); $^{13}C$ NMR ($CD_3OD$, 75 MHz) δ28.8 (3 C), 34.1, 37.9, 80.2, 158.3, 170.8; MS (+CI). 205 [M+1]$^+$; $M_r$(+CI) 205.117 83 [M+1]$^+$ (calcd for $C_8H_{17}N_2O_4$, 205.118 83). Anal. ($C_8H_{16}N_2O_4 \cdot 0.1H_2O$) C, 46.64; H, 7.92; N, 13.60. Found C, 46.79; H, 7.97; N, 13.28.

N-(tert-Butoxycarbonyl)-D-methionone Hydroxamic Acid (22)

Yield, 31%; $R_f$=0.47 (10% MeOH—$CHCl_3$); mp 129-131° C.; $^1H$ NMR ($CD_3OD$, 300 MHz) δ1.44 (s, 9H), 1.83-2.00 (m, 2H), 2.08 (s, 3H), 2.47-2.54 (m, 2H), 4.09 (t, J=6.3 Hz, 1H); $^{13}C$ NMR ($CD_3OD$, 75 MHz) δ15.3, 28.7 (3 C), 31.1, 33.1, 52.9, 80.7, 157.7, 171.4; MS (+CI) 265 [M+1]$^+$; $M_r$ (+CI) 265.122 48 [M+1]$^+$ (calcd for $C_{10}H_{21}N_2O_4S$, 265.122 20).

General Coupling Procedure Using DCC for the BOC-Hydroxamic Acids (19-20)

To a THF (2 mL/1 mmol of amino acid) solution of the BOC-amino acid (1 equiv) was added a solution of hydroxylamine hydrochloride (2 equiv) in a $H_2O$ (4 mL/1 mmol of hydroxylamine). The pH was maintained at 4.5-5.0 while a THF (3 mL/1 mmol of DCC) solution of DCC (2 equiv) was added with stirring (1-5 h). The solid was filtered and the filtrate was concentrated in vacuo. The residue was purified by PTLC (EtOAc/hexanes) to afford the desired hydroxamic acid.

O-Methyl-N-(tert-butoxycarbonyl)-D-serine Hydroxamic Acid (19)

Yield, 46%; $R_f$=0.41 (10% MeOH—$CHCl_3$); mp 83-85° C. (lit.[4] mp 84-86° C.); $^1H$ NMR ($CD_3OD$, 400 MHz) δ1.45 (s, 9H), 3.69 (s, 3H), 3.70 (d, J=3.9 Hz, 2H), 4.02 (t, J=3.9 Hz, 1H); $^{13}C$ NMR ($CD_3OD$, 100 MHz) δ28.7 (3 C), 56.1, 63.0, 64.4, 80.9, 157.7, 170.0; MS (+CI) 235 [M+1]$^+$; $M_r$ (+CI) 235.128 46 [M+1]$^+$ (calcd for $C_9H_{19}N_2O_5$, 235.129 39).

O-Benzyl-N-(tert-butoxycarbonyl)-D-serine Hydroxamic Acid (20)

Yield, 54%; $R_f$=0.66 (10% MeOH—$CHCl_3$); mp 128-130° C. (lit.[5] mp 130-131° C. for L-isomer); IR (KBr) 3359, 3190, 2993, 2933, 1710, 1668, 1512, 1400, 1252, 1168, 1067 cm$^{-1}$; $^1H$ NMR ($CD_3OD$, 300 MHz) δ1.44 (s, 9H), 3.67 (d, J=5.4 Hz, 2H), 4.03 (t, J=5.4 Hz, 1H), 4.84 (s, 2H), 7.33-7.45 (m, 5H); $^{13}C$ NMR ($CD_3OD$, 75 MHz) δ28.7 (3 C), 56.1, 63.2, 79.2, 80.9, 129.5, 129.7 (2 C), 130.5 (2 C), 136.9, 157.6, 170.2; MS (+CI) 311 [M+1]$^+$; $M_r$ (+CI) 311.160 52 [M+1]$^+$ (calcd for $C_{15}H_{23}N_2O_5$, 311.160 69).

N-(tert-Butoxycarbonyl)-D-serine Hydroxamic Acid (21)

A solution of 20 (137 mg, 0.44 mmol) in EtOH (7 mL) containing 10% Pd—C (46 mg) was hydrogenated at 1 atm (1.5 h). The catalyst was filtered and the filtrate was concentrated in vacuo, and then crystallized with isopropyl ether to afford 21 as a solid. Yield, 81%; $R_f$=0.19 (10% MeOH—$CHCl_3$); mp 108-110° C. (lit.[6] mp 106-112° C. for L-isomer); IR (KBr) 3421, 3318, 2871, 1726, 1670, 1514, 1370, 1243, 1160 cm$^{-1}$; $^1H$ NMR ($CD_3OD$, 300 MHz) δ1.44 (s, 9H), 3.69 (d, J=5.4 Hz, 2H), 4.06 (t, J=5.4 Hz, 1H); $^{13}C$ NMR ($CD_3OD$, 75 MHz) δ28.7 (3 C), 56.1, 63.2, 80.9, 157.6, 170.1; MS (+CI) 221 [M+1]$^+$; $M_r$ (+CI) 221.113 90 [M+1]$^+$ (calcd for $C_8H_{17}N_2O_5$, 221.113 74).

General Procedure for Removal of the BOC Group.

(1) Using HCl/EtOAc.
AnEtOAC (3.8-4.0 mL/1 mmol of BOC-hydroxamic acid) solution of HCl prepared from acetyl chloride (8 equiv) and EtOH (8 equiv) was added to the BOC-hydroxamic acid (1 equiv), and the reaction was stirred at room temperature (15-18 h). The solid was filtered, and washed with EtOAc to afford the hydroxamic acid as a HCl salt.

(2) Using Trifluoroacetic Acid.
The BOC-hydroxamic acid (1 equiv) was dissolved in TFA (1.0-1.2 mL/1 mmol of the BOC-hydroxamic acid) and stirred at room temperature (30 min). The TFA salt was precipitated by addition of ethyl ether or isopropyl ether. The solid was filtered and washed with isopropyl ether (5 mL), and dried in vacuo to yield the hydroxamic acid as a TFA salt. Compounds 3, 5 and 9 were obtained as either an oil or a semi-solid.

Glycine Hydroxamic Acid Hydrochloride (2)

Yield, 73%; mp 103-106° C. (lit.[7] mp 108-109° C.); $^1H$ NMR ($CD_3OD$, 300 MHz) δ3.92 (s, 2H); $^{13}C$ NMR ($CD_3OD$, 75 MHz) δ39.5, 164.9; MS (+CI) 91 [(M—HCl)+1]$^+$; $M_r$ (+CI) 91.050 60 [(M—HCl)—H]$^+$ (calcd for $C_2H_7N_2O_2$, 91.050 75).

N-Methylglycine Hydroxamic Acid Trifluoroacetic Acid (3).[1]

Yield, 85% as a semi-solid; $^1H$ NMR ($CD_3OD$, 300 MHz) δ3.25 (s, 3H), 3.93 (s, 2H); $^{13}C$ NMR ($CD_3OD$, 75 MHz) δ36.4, 40.7, 163.3, 167.5; MS (+CI) 105 [(M—TFA)+1]$^+$; $M_r$ (+CI) 104.058 41 [M—TFA]$^+$ (calcd for $C_3H_8N_2O_2$, 104.058 58).

O-Methylglycine Hydroxamic Acid Trifluoroacetic Acid (4)

Yield, 78%; mp 114-116° C. (lit.[1] mp 113-114° C.); $^1H$ NMR (DMSO-$d_6$, 300 MHz) δ3.49 (s, 2H), 3.64 (s, 3H), 3.84 (s, 1H), 8.38 (br s, 2H); $^{13}C$ NMR (DMSO-$d_6$, 75 MHz) δ38.1, 63.5, 163.1; MS (+CI) 105 [(M—TFA)+1]$^+$; $M_r$ (+CI) 105.065 91 [(M—TFA)+1]$^+$ (calcd for $C_3H_9N_2O_2$, 105.066 40).

N,O-Methylglycine Hydroxamic Acid Trifluoroacetic Acid (5).[1]

Yield, 81% as a semi-solid; $^1H$ NMR ($CD_3OD$, 300 MHz) δ3.23 (s, 3H), 3.77 (s, 3H), 3.98 (s, 2H); $^{13}C$ NMR ($CD_3OD$, 75 MHz) δ32.5, 40.8, 62.2, 168.2; MS (+CI) 119 [(M—TFA)+1]$^+$; $M_r$ (+CI) 118.074 31 [M—TFA]$^+$ (calcd for $C_4H_{10}N_2O_2$, 118.074 23).

D-Alanine Hydroxamic Acid Hydrochloride (6)

Yield, 95%; mp 179-181° C. (lit.[8] mp 183-184° C. for the racemate); IR (KBr) 3177, 2997, 1677, 1566, 1532, 1487, 1389, 1180, 1037 cm$^{-1}$; $^1H$ NMR ($CD_3OD$, 300 MHz) δ1.50 (d, J=7.2 Hz, 3H), 3.88 (q, J=7.2 Hz, 1H); $^{13}C$ NMR ($CD_3OD$, 75 MHz) δ17.8, 48.4, 168.4; MS (+CI) 105 [(M—HCl)+1]$^+$; $M_r$ (+CI) 105.065 98 [(M—HCl)+1]$^+$ (calcd for $C_3H_9N_2O_2$, 105.066 40). Anal. ($C_3H_8N_2$.1.1HCl.0.05 EtOAc) C, 25.86; H, 6.44; N, 18.85. Found C, 25.78; H, 6.46; N, 18.87.

L-Alanine Hydroxamic Acid Hydrochloride (7)

Yield, 94%; mp 178-180° C. (lit.[8] mp 183-184° C. for the racemate); IR (KBr) 3180, 1681, 1610, 1568, 1492, 1393, 1270, 1213, 1138, 1039 cm$^{-1}$; $^1H$ NMR ($CD_3OD$, 300 MHz) δ1.50 (d, J=7.2 Hz, 3H), 3.89 (q, J=7.2 Hz, 1H); $^{13}C$ NMR ($CD_3OD$, 75 MHz) δ17.8, 48.4, 168.4; MS (+CI) 105 [(M—HCl)+1]$^+$; $M_r$ (+CI) 105.066 02 [(M—HCl)+1]$^+$ (calcd for $C_3H_9N_2O_2$, 105.066 40). Anal. ($C_3H_8N_2O_2$.1.1HCl.0.1 EtOAC) C, 26.69; H, 6.52; N, 18.30. Found C, 26.52; H, 6.50; N, 18.61.

β-Alanine Hydroxamic Acid Hydrochloride (8)

Yield, 85%; mp 140-142° C. (lit.[7] mp 144° C.), $^1H$ NMR ($CD_3OD$, 300 MHz) δ2.33 (t, J=6.6 Hz, 2H), 3.01 (t, J=6.6

Hz, 2H); $^{13}$C NMR (CD$_3$OD, 75 MHz) δ30.1, 37.1, 169.4; MS (+CI) 105 [(M—HCl)+1]$^+$; M$_r$ (+CI) 105.065 88 [(M—HCl)+1]$^+$ (calcd for C$_3$H$_9$N$_2$O$_2$, 105.066 40).

O-Methyl-D-serine Hydroxamic Acid Trifluoroacetic Acid (9)

Yield, 80% as a semi-solid; IR (neat) 3450, 1681, 1525, 1439, 1142, 1052 cm$^{-1}$; $^1$H NMR (CD$_3$OD, 400 MHz) δ3.74 (s, 3H), 3.78-3.92 (m, 2H), 4.37 (t, J=3.9 Hz, 1H); $^{13}$C NMR (CD$_3$OD, 100 MHz) δ54.3, 61.6, 64.7, 165.6; MS (+CI) 135 [(M—TFA)+1]$^+$; M$_r$ (+CI) 135.076 18 [(M—TFA)+1]$^+$ (calcd for C$_4$H$_{11}$N$_2$O$_3$, 135.076 96). Anal. (C$_4$H$_{10}$N$_2$O$_3$.1.1 CF$_3$CO$_2$H.0.2H$_2$O) C, 28.30; H, 4.40; N, 10.64. Found C, 28.24; H, 4.60; N, 10.46.

Scheme 1. General Scheme for the Hydroxamic Acids (10-12)

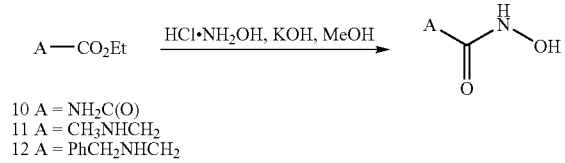

10 A = NH$_2$C(O)
11 A = CH$_3$NHCH$_2$
12 A = PhCH$_2$NHCH$_2$

General Coupling Procedure for the Hydroxamic Acid (10-12)

To an absolute MeOH (0.5-1.0 mL/1 mmol of ethyl ester) solution of ethyl ester (1 equiv) was added an absolute MeOH (0.7-1.0 mL/1 mmol of hydroxylamine hydrochloride) solution of hydroxylamine prepared from hydroxylamine hydrochloride (1.5 equiv) and KOH (1.5 equiv). The reaction mixture was stirred at 0-5° C. (12-15 h), filtered, and then the solid washed with H$_2$O (10 mL) to afford the desired hydroxamic acid.

N-Hydroxyoxalamide (10)

Yield, 62%; R$_f$=0.11 (25% MeOH—CHCl$_3$); mp 158-159° C. (lit.[9] mp 140-141° C., lit.[10] mp 159° C.); $^1$H NMR (DMSO-d$_6$, 300 MHz) δ7.75 (s, 1H), 8.53 (br s, 2H), the remaining protons were not detected; $^{13}$C NMR (DMSO-d$_6$, 75 MHz) δ157.1, 162.0; MS (+CI) 105 [M+1]$^+$; M$_r$ (+CI) 105.029 86 [M+1]$^+$ (calcd for C$_2$H$_5$N$_2$O$_3$, 105.030 01). Anal. (C$_9$H$_{12}$N$_2$O$_2$) C, 59.99; H, 6.71; N, 15.55. Found C, 59.71; H, 6.75; N, 15.37.

Sarcosine Hydroxamic Acid (11)

Yield, 58%; R$_f$=0.06 (25% MeOH—CHCl$_3$); mp 140-141° C. (lit.[11] mp 140-141° C.); $^1$H NMR (DMSO-d$_6$, 300 MHz) δ2.21 (s, 3H), 2.96 (s, 2H), the remaining protons were not detected; $^{13}$C NMR (DMSO-d$_6$, 75 MHz) δ35.7, 51.8, 167.7; MS (+CI) 105 [M+1]$^+$; M$_r$ (+CI) 105.066 07 [M+1]$^+$ (calcd for C$_3$H$_9$N$_2$O$_2$, 105.066 40).

N-Benzylglycine Hydroxamic Acid (12)

Yield, 53%; R$_f$=0.32 (25% MeOH—CHCl$_3$); mp 142-143° C.; IR (KBr) 3160, 1680, 1609, 1465, 1353, 1284, 1199, 1022 cm$^{-1}$; $^1$H NMR (DMSO-d$_6$, 300 MHz) δ3.00 (s, 2H), 3.65 (s, 2H), 7.21-7.32 (m, 5H); $^{13}$C NMR (DMSO-d$_6$, 75 MHz) δ49.0, 52.3, 126.6, 127.9 (2 C), 128.1 (2 C), 140.2, 167.7; MS (+CD) 181 [M+1]$^+$; M$_r$ (+CI) 181.098 01 [M+1]$^+$ (calcd for C$_9$H$_{13}$N$_2$O$_2$, 181.097 70). Anal. (C$_9$H$_{12}$N$_2$O$_2$) C, 59.99; H, 6.71; N, 15.55. Found C, 59.71; H, 6.75; N, 15.37.

REFERENCES

The following references were cited herein:

1) Johnson, G.; Boxer, P. A.; Drummond, J. T.; Boyd, D. K.; Anderson, R. J. Identification and Evaluation of O-Alkyl Substituted Hydroxamic Acids as Potent in vitro Inhibitors of the Hepatic Glycine Cleavage System and Investigation of Their Action on in vivo Central Nervous System Glycine Concentration. *Arzneim-Forsch./Drug Res.*, 1989, 39, 432-437.

2) Welch, J. T.; Lin J. Fluoroolefin Containing Dipeptide Isosteres as Inhibitors of Dipeptidyl Peptidase IV (CD26). *Tetrahedron*, 1996, 52, 291-304.

3) Lee, J.; Kang, M. K.; Chun, M. W.; Jo, Y. J.; Kwak, J. H.; Kim, S. Methionine Analogues as Inhibitors of Methionyl-tRNA Synthetase. *Bioorg. Med. Chem. Lett.*, 1998, 8, 3511-3514.

4) Floyd, D. M.; Fritz, A. W.; Pluscec, J.; Weaver, E. R.; Cimarusti, C. M. Monobactams. Preparation of (S)-3-Amino-2-oxoazetidine-1-sulfonic Acids from L-α-Amino-β-hydroxy Acids via Their Hydroxamic Esters. *J. Org. Chem.*, 1982, 47, 5160-5167.

5) Mattingly, P. G.; Miller, M. J. Titanium Trichloride Reduction of Substituted N-Hydroxy-2-azetidinones and Other Hydroxamic Acids. *J. Org. Chem.*, 1980, 45, 410-415.

6) Gordon, E. M.; Ondetti, M. A.; Pluscec, J.; Cimarusti, C. M.; Bonner, D. P.; Sykes, R. B. O-Sulfated β-Lactam Hydroxamic Acids (Monosulfactams). Novel Monocyclic β-Lactam Antibiotics of Synthetic Origin. *J. Am. Chem. Soc.*, 1982, 104, 6053-6060.

7) Matveev, B. V.; Tsybaeva, G. G. Synthesis and Polarographic Reduction of Aliphatic Amino Hydroxamic Acids. *J. Gen. Chem. USSR (Engl. Transl.)*, 1964, 34, 2512-2516.

8) Knobler, Y.; Bittner, S.; Frankel, M. Reaction of N-Carboxy-α-Amino-acid Anhydrides with Hydrochlorides of Hydroxylamine, O-Alkylhydroxylamines, and Amines; Syntheses of Amino-hydroxamic Acids, Amido-oxy-peptides, and α-Amino-acid Amides. *J. Chem. Soc.*, 1964, 3941-3951.

9) Petyunin, G. P.; Erling, R.; Naumann, K.; Kulikova, D. A.; Ostapchuk, N. V. Amides and Hydrazides of Oxalic Acid XXXVII. Synthesis and Biological Activity of Substituted Carbamidohydroxamic Acids. *Pharm. Chem. J. (Engl. Transl.)*, 1978, 12, 780-782.

10) Houben; Schmidt. *Chem Ber.*, 1913, 46, 3622.

11) Harmon, R. E.; Rizzo, V. L.; Gupta, S. K. Synthesis of 3-Hydroxy-4-Imidazolidinones (1a, b). *J. Heterocycl. Chem.* 1970, 7, 439-442.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. An anti-mycobacterial composition comprising a therapeutically effective amount of at least one compound of the formula (I):

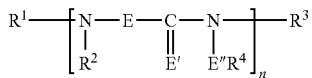

or pharmaceutically acceptable salts thereof and at least one hydroxylamine having the formula (II):

$$H_2N-OR \qquad (II)$$

where:
$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2CR^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;
E" is O;
n is an integer having a value between 1 and 4; and
R is selected from the group consisting of an hydrogen atom, a C1 alkyl group, C2 alkyl group, C3 alkyl group and C4 alkyl group.

2. The composition of claim 1, wherein the at least one compound of formula (I) is optically pure, a racemic mixture, or an optical active mixture of pure enantiomers.

3. The composition of claim 1, where at least one compound of formula (I) is selected from the group consisting of glycine hydroxamic acid, glycine hydroxamic acid hydrochloride, glycine hydroxamic trifluoracetic acid, O-methylglycine hydroxamic acid trifluoracetic acid, D-alanine hydroxamic acid hydrochloride, L-alanine hydroxamic acid hydrochloride, N-hydroxyoxalamide, sarcosine hydroxamic acid, and D-methionine hydroxamic acid.

4. The composition of claim 1, wherein the at least one compound of formula (II) is selected from the group consisting of hydroxylamine, methylhydroxylamine and ethylhydroxylamine.

5. The composition of claim 1, wherein the at least one compound of formula (II) is hydroxylamine.

6. The composition of claim 1, wherein $R^1$, $R^2$, $R^3$, $R^4$, $R^5$, $R^6$ and $R^7$ are independently unsubstituted or substituted, if substituted the substituents comprise at least one electron withdrawing substituent or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

7. The composition of claim 6, wherein $R^8$, $R^9$ and $R^{10}$ are independently unsubstituted or substituted with at least one electron withdrawing or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

8. An anti-mycobacterial composition comprising a therapeutically effective amount of at least one compound of the formula (I):

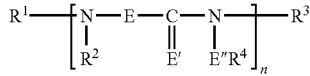

or pharmaceutically acceptable salts thereof and at least one hydroxylamine having the formula (II):

$$H_2N-OR \qquad (II)$$

where:
R is selected from the group consisting of an hydrogen atom, a C1 alkyl group, C2 alkyl group, C3 alkyl group and C4 alkyl group;
$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2CR^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is O;

n is an integer having a value between 1 and 4; and where a wt. % ratio of compounds of formula (I) to compounds of formula (II) is between about 100:1 and about 1:1.

9. The composition of claim 8, wherein the at least one compound of formula (I) is optically pure, a racemic mixture, or an optical active mixture of pure enantiomers.

10. The composition of claim 8, where at least one compound of formula (I) is selected from the group consisting of glycine hydroxamic acid, glycine hydroxamic acid hydrochloride, glycine hydroxamic trifluoracetic acid, O-methylglycine hydroxamic acid trifluoracetic acid, D-alanine hydroxamic acid hydrochloride, L-alanine hydroxamic acid hydrochloride, N-hydroxyoxalamide, sarcosine hydroxamic acid, and D-methionine hydroxamic acid.

11. The composition of claim 8, wherein the at least one compound of formula (II) is selected from the group consisting of hydroxylamine, methylhydroxylamine and ethylhydroxylamine.

12. The composition of claim 8, wherein the at least one compound of formula (II) is hydroxylamine.

13. The composition of claim 8, wherein $R^1$, $R^2$, $R^3$, $R^4$, $R^5$, $R^6$ and $R^7$ are independently unsubstituted or substituted, if substituted the substituents comprise at least one electron withdrawing substituent or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

14. The composition of claim 13, wherein $R^8$, $R^9$ and $R^{10}$ are independently unsubstituted or substituted with at least one electron withdrawing or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

15. The composition of claim 8, wherein the wt. % ratio of compounds of formula (I) to compounds of formula (II) is between about 100:1 and about 10:1 and wherein the therapeutically effective amount is between about 125 μg/mL and about 1 μg/mL for each hydroxamate used in the composition and between about 125 μg/mL and about 1 μg/mL for each hydroxylamine used in the composition.

16. A method for treating mycobacterial infections in animals comprising the step of:

administering to an animal including a human on an individual, continuous, periodic, or intermittent basis or according to an individual, continuous, periodic, or intermittent administration protocol, an therapeutically effective amount composition having anti-mycobacterial activity including at least one compound of formula (I):

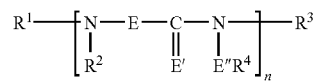

or pharmaceutically acceptable salts thereof and at least one hydroxylamine having the formula (II):

where:

$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E is selected from the group consisting of $CR^5(R^6)$, $CH_2CR^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;

E' is selected from the group consisting of O, S, or $NR^7$;

E" is O;

n is an integer having a value between 1 and 4; and

R is selected from the group consisting of an hydrogen atom, a C1 alkyl group, C2 alkyl group, C3 alkyl group and C4 alkyl group.

17. The method of claim 16, wherein the at least one compound of formula (I) is optically pure, a racemic mixture, or an optical active mixture of pure enantiomers.

18. The method of claim 16, where at least one compound of formula (I) is selected from the group consisting of glycine hydroxamic acid, glycine hydroxamic acid hydrochloride, glycine hydroxamic trifluoracetic acid, O-methylglycine hydroxamic acid trifluoracetic acid, D-alanine hydroxamic acid hydrochloride, L-alanine hydroxamic acid hydrochloride, N-hydroxyoxalamide, sarcosine hydroxamic acid, and D-methionine hydroxamic acid.

19. The method of claim 16, wherein the at least one compound of formula (II) is selected from the group consisting of hydroxylamine, methylhydroxylamine and ethylhydroxylamine.

20. The method of claim 16, wherein the at least one compound of formula (II) is hydroxylamine.

21. The method of claim 16, wherein $R^1$, $R^2$, $R^3$, $R^4$, $R^5$, $R^6$ and $R^7$ are independently unsubstituted or substituted, if substituted the substituents comprise at least one electron withdrawing substituent or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, $NOH$, $NOR^8$, $C(O)R^8$, $CO_2H$, $CO_2R^8$, $CN$, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

22. The method of claim 21, wherein $R^8$, $R^9$ and $R^{10}$ are independently unsubstituted or substituted with at least one electron withdrawing or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, $NOH$, $NOR^8$, $C(O)R^8$, $CO_2H$, $CO_2R^8$, $CN$, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

23. The method of claim 16, wherein a wt. % ratio of compounds of formula (I) to compounds of formula (II) is between about 100:1 and about 1:1 and wherein the therapeutically effective amount is between about 125 µg/mL and about 1 µg/mL for each hydroxamate used in the composition and between about 125 µg/mL and about 1 µg/mL for each hydroxylamine used in the composition.

24. A method for treating mycobacterial infections in animals comprising the step of:
administering to an animal including a human on an individual, continuous, periodic, or intermittent basis or according to an individual, continuous, periodic, or intermittent administration protocol, an therapeutically effective amount composition having anti-mycobacterial activity including at least one compound of formula (I):

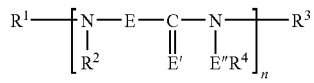

or pharmaceutically acceptable salts thereof, or pharmaceutically acceptable salts thereof and at least one hydroxylamine having the formula (II):

 (II)

where:
R is selected from the group consisting of an hydrogen atom, a C1 alkyl group, C2 alkyl group, C3 alkyl group and C4 alkyl group;
$R^1$, $R^2$, $R^3$ and $R^4$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
E is selected from the group consisting of $CR^5(R^6)$, $CH_2CR^5(R^6)$, and $CR^5(R^6)CH_2$, where $R^5$ and $R^6$ are independently selected from the group consisting of hydrogen, linear or branched lower alkyl, linear or branched lower alkenyl, linear or branched lower alkynyl, linear or branched aryl lower alkyl, linear or branched aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof;
E' is selected from the group consisting of O, S, or $NR^7$;
E" is O; and
n is an integer having a value between 1 and 4,
where a wt. % ratio of compounds of formula (I) to compounds of formula (II) is between about 100:1 and about 1:1.

25. The method of claim 24, wherein the at least one compound of formula (I) is optically pure, a racemic mixture, or an optical active mixture of pure enantiomers.

26. The method of claim 24, where at least one compound of formula (I) is selected from the group consisting of glycine hydroxamic acid, glycine hydroxamic acid hydrochloride, glycine hydroxamic trifluoracetic acid, O-methylglycine hydroxamic acid trifluoracetic acid, D-alanine hydroxamic acid hydrochloride, L-alanine hydroxamic acid hydrochloride, N-hydroxyoxalamide, sarcosine hydroxamic acid, and D-methionine hydroxamic acid.

27. The method of claim 24, wherein the at least one compound of formula (II) is selected from the group consisting of hydroxylamine, methylhydroxylamine and ethylhydroxylamine.

28. The method of claim 24, wherein the at least one compound of formula (II) is hydroxylamine.

29. The method of claim 24, wherein $R^1$, $R^2$, $R^3$, $R^4$, $R^5$, $R^6$ and $R^7$ are independently unsubstituted or substituted, if substituted the substituents comprise at least one electron withdrawing substituent or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, $NOH$, $NOR^8$, $C(O)R^8$, $CO_2H$, $CO_2R^8$, $CN$, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

30. The method of claim 29, wherein $R^8$, $R^9$ and $R^{10}$ are independently unsubstituted or substituted with at least one electron withdrawing or at least one electron donating substituent selected from the group consisting of $OR^8$, $SR^8$, $S(O)R^8$, $S(O)_2R^8$, $NH_2$, $NHR^8$, $NR^8(R^9)$, $NHNH_2$, $N(R^8)NH_2$, $N(R^8)N(R^9)H$, $N(R^8)N(R^9)(R^{10})$, NOH, $NOR^8$, $C(O)R^8$, $CO_2H$, $CO_2R^8$, CN, $C(O)NH_2$, $C(O)NHR^8$, $C(O)NR^8(R^9)$, $OC(O)NH_2$, $OC(O)NHR^8$, $OC(O)NR^8(R^9)$, $C(NR^8)N(H)R^9$, $C(NR^8)NR^9(R^{10})$ and mixtures or combinations thereof, where $R^8$, $R^9$ and $R^{10}$ are independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof.

31. The method of claim 24, wherein the wt. % ratio of compounds of formula (I) to compounds of formula (II) is between about 100:1 and about 10:1 and wherein the therapeutically effective amount is between about 125 μg/mL and about 1 μg/mL for each hydroxamate used in the composition and between about 125 μg/mL and about 1 μg/mL for each hydroxylamine used in the composition.

32. The composition of claim 1, wherein a wt. % ratio of compounds of formula (I) to compounds of formula (II) is between about 100:1 and about 1:1 and wherein the therapeutically effective amount is between about 125 μg/mL and about 1 μg/mL for each hydroxamate used in the composition and between about 125 μg/mL and about 1 μg/mL for each hydroxylamine used in the composition.

* * * * *